United States Patent [19]

Lipps et al.

[11] 4,231,871

[45] Nov. 4, 1980

[54] ARTIFICIAL KIDNEY AND METHOD FOR MAKING SAME

[75] Inventors: Bennie J. Lipps, Walnut Creek, Calif.; William P. Murphy, Jr., Miami, Fla.; Frank W. Mather, III, Lafayette, Calif.

[73] Assignee: Cordis Dow Corp., Miami, Fla.

[21] Appl. No.: 931,229

[22] Filed: Aug. 7, 1978

Related U.S. Application Data

[62] Division of Ser. No. 805,601, Jun. 10, 1977.

[51] Int. Cl.³ .................... B01D 31/00; A61M 1/03
[52] U.S. Cl. ........................................ 210/87; 210/90; 210/321 B; 210/96.2
[58] Field of Search ........... 210/321 A, 321 B, 321 R, 210/96 M, 90, 87

[56] References Cited

U.S. PATENT DOCUMENTS

| | | | |
|---|---|---|---|
| 3,441,136 | 4/1969 | Serfass et al. | 210/96 M X |
| 3,640,393 | 2/1972 | Hurtig | 210/321 R |
| 3,774,762 | 11/1973 | Lichtenstein | 210/96 M X |
| 3,946,731 | 3/1976 | Lichtenstein | 210/90 X |
| 3,963,622 | 6/1976 | Baudet et al. | 210/321 A X |
| 4,054,527 | 10/1977 | Esmohd | 210/321 B |
| 4,127,481 | 11/1978 | Malchesky et al. | 210/321 R X |

FOREIGN PATENT DOCUMENTS 2267138  11/1975  France ................. 210/321 R

*Primary Examiner*—Frank A. Spear, Jr.
*Attorney, Agent, or Firm*—Neal A. Waldrop

[57] ABSTRACT

An improved one-piece, integral hollow fiber artificial kidney and a semi-continuous method for making such kidneys and other apparatus of the hollow fiber separatory-type.

15 Claims, 17 Drawing Figures

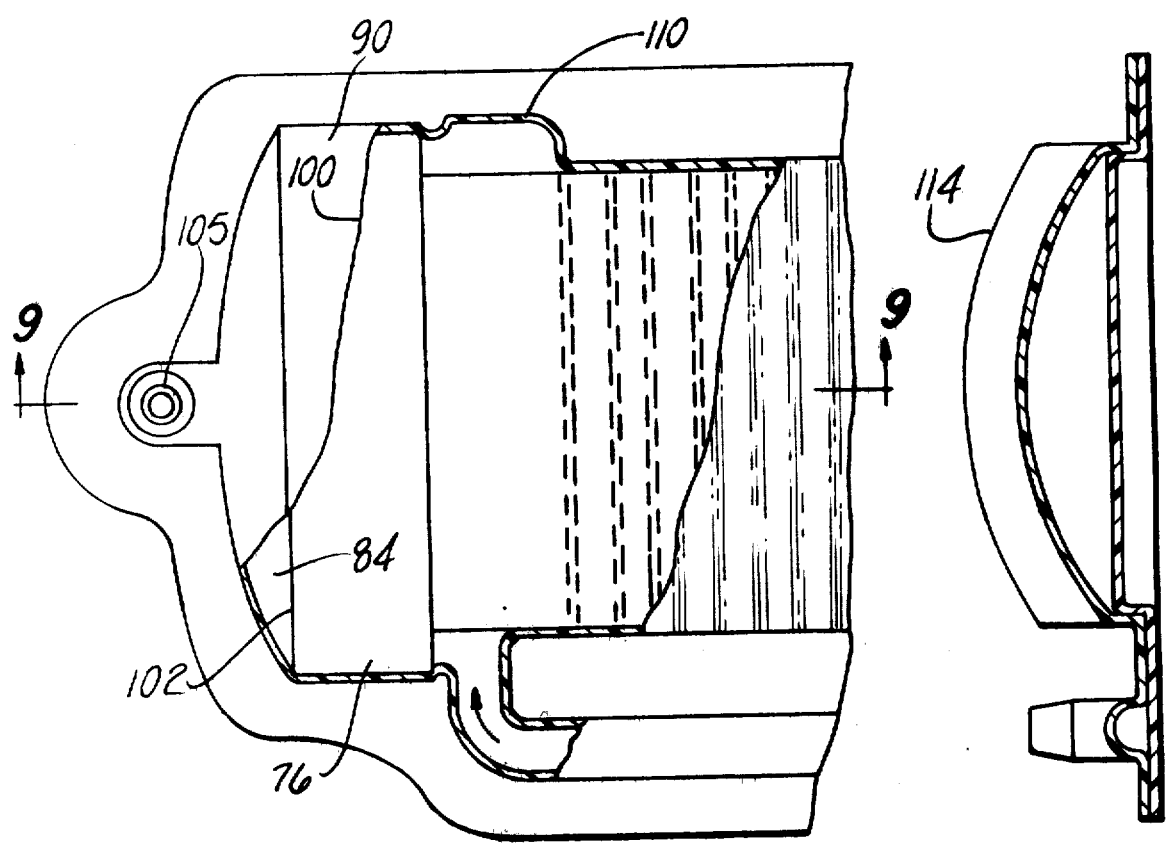
Fig-7
Fig-8
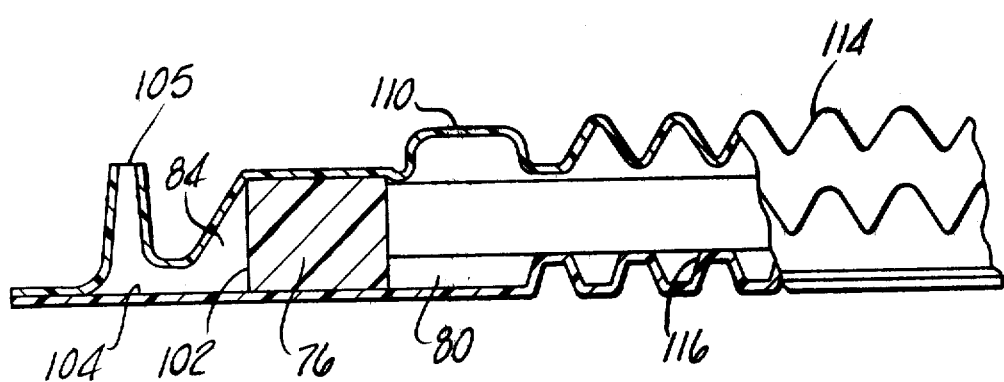
Fig-9

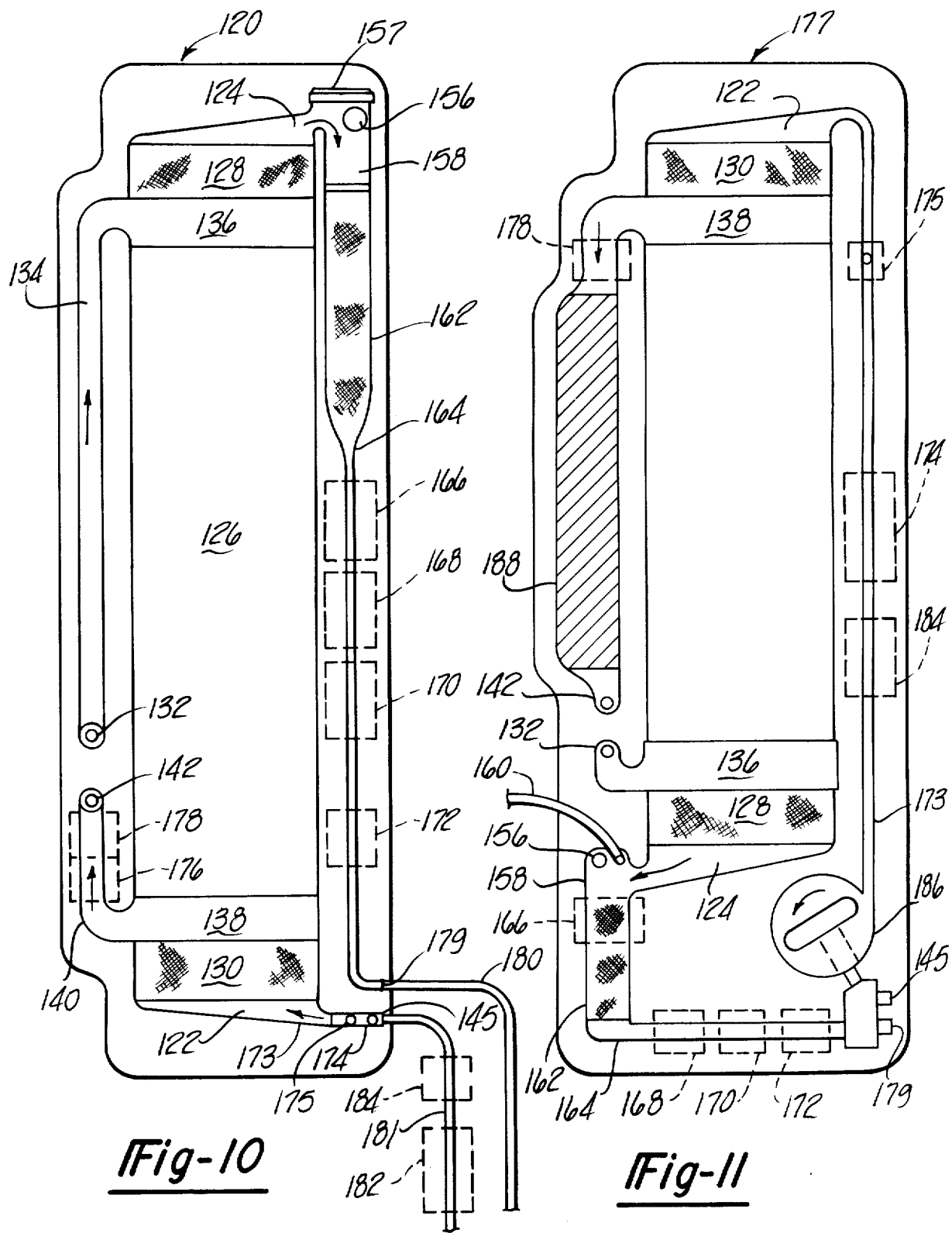

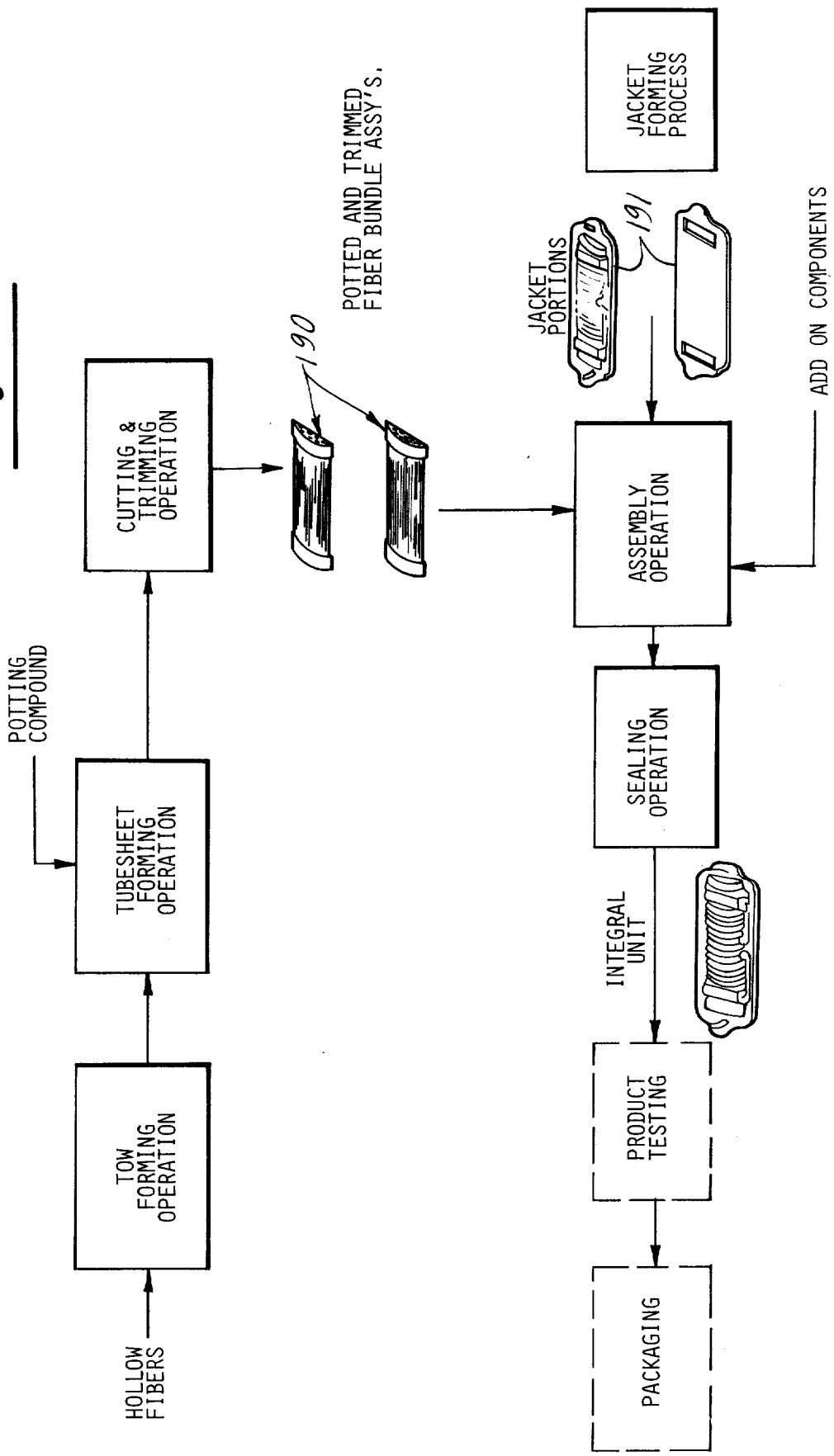

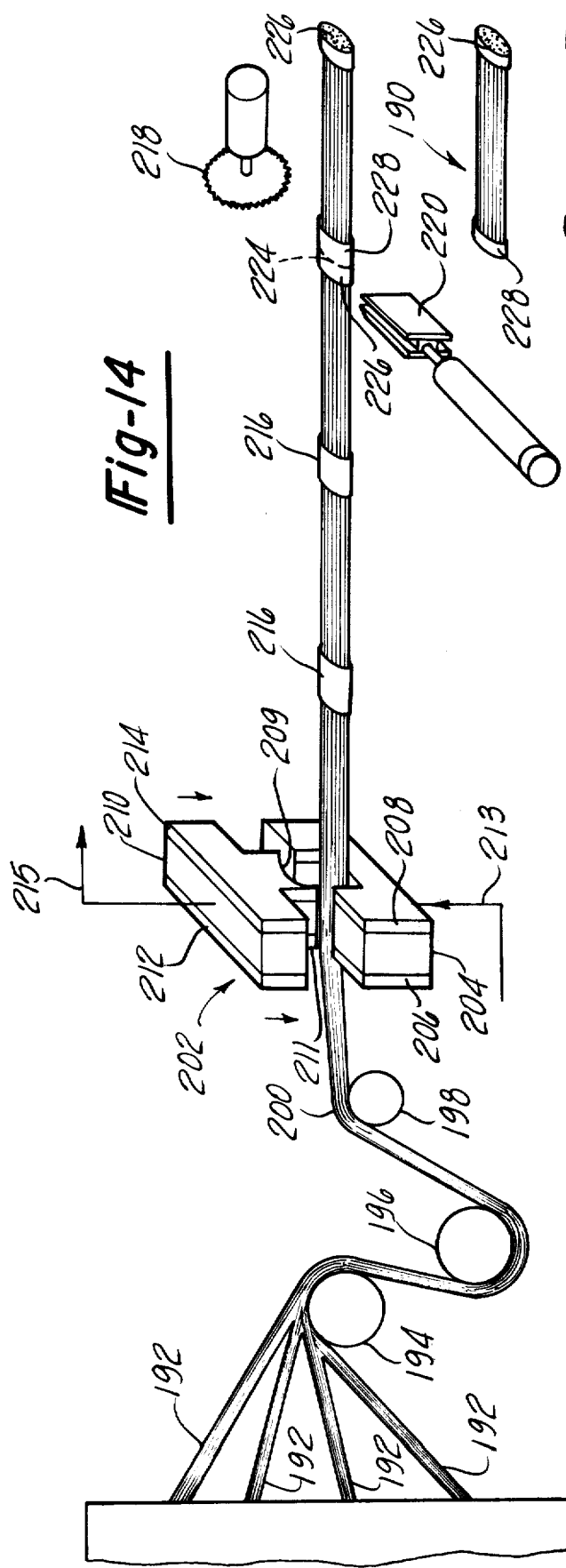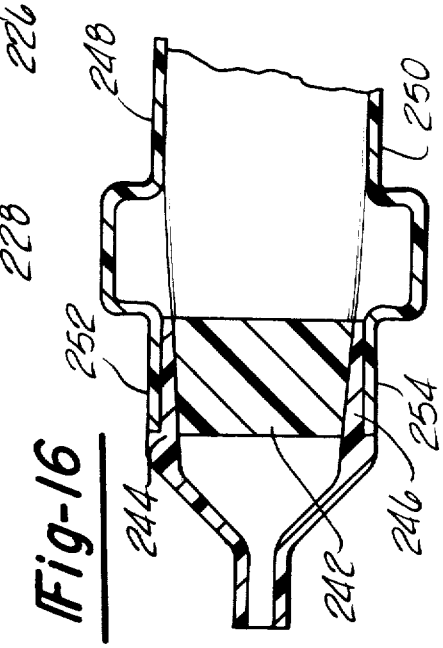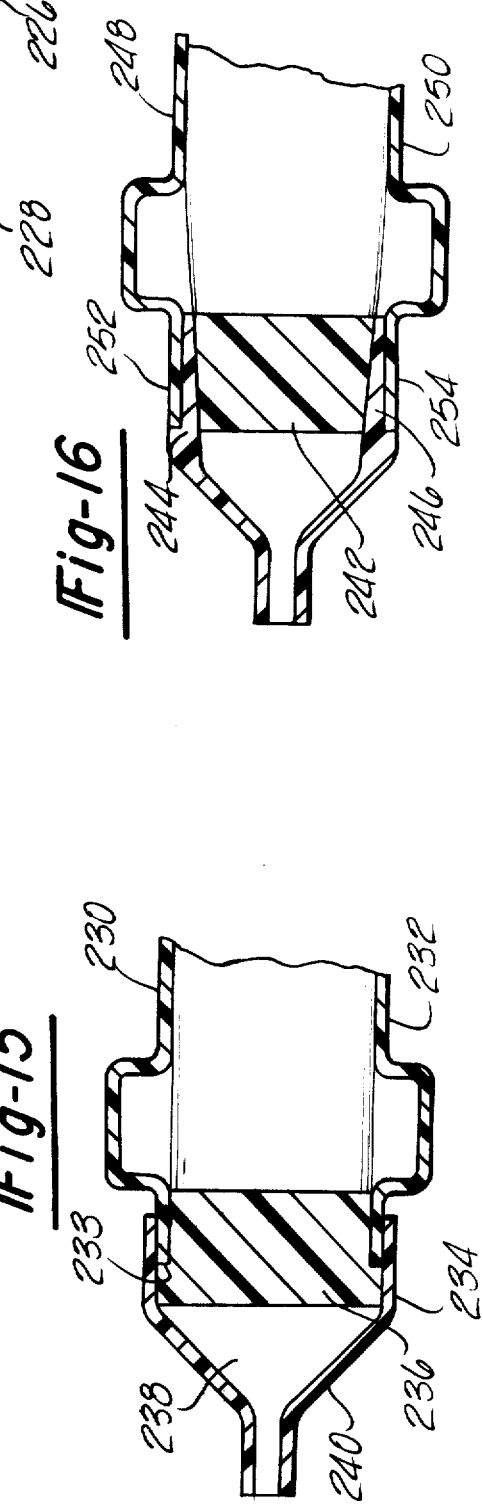

ARTIFICIAL KIDNEY AND METHOD FOR MAKING SAME

CROSS-REFERENCE TO RELATED APPLICATIONS

This application is a division of application Ser. No. 805,601, filed June 10, 1977 and is being filed pursuant to 35 U.S.C. 121.

BACKGROUND OF THE INVENTION

This invention relates to improved hollow fiber artificial kidneys or hemodialyzers and to a method for the manufacture thereof.

Intermittent dialysis of patients having acute or chronic renal failure has greatly increased in recent years. Flat plate and coil type dialyzers have been replaced, increasingly, by hollow fiber dialyzers of the type disclosed in De Wall U.S. Pat. No. 2,972,349 and Mahon U.S. Pat. No. 3,228,876 and available commercially from Cordis Dow Corporation. Such hollow fiber dialyzers contain thousands of small diameter hollow fibers which are typically cellulose and the product of the cuproammonium process or the process of Lipps U.S. Pat. No. 3,546,209. These fibers are mounted within a tubular dialysis chamber, have a length less than about ten inches and their open ends terminate in spaced apart blood chambers that are formed by headers which are secured to each end of the dialysis chamber by internally threaded caps. The manufacture of such hollow fiber artificial kidneys is difficult and undesirably expensive because of the complexities inherent in the fabrication of the separate components and their subsequent assembly into composite kidney form. Because sterility of all surfaces which contact the blood while it is outside the body during dialysis is an absolute necessity, and it is difficult to sterilize a used artificial kidney for possible re-use, most artificial kidneys are used only once and discarded. Cheaper artificial kidneys are therefore highly desireable.

Those familiar with current commercial systems used in dialysis clinics have criticized conventional use of long blood lines which transport the blood from an artery through racetrack sections to measure blood flow rate, through blood pump tubing, past drip chambers, infusion sites, blood sampling sites and back from the kidney to the patient. Such lines are clumsy to handle, and complicated to assemble, sterilize and maintain. Thus, it has long been recognized that supplemental segments of the extracorporeal circuit, particularly long blood lines, are less than satisfactory and need improvement.

Although current hollow fiber artificial kidneys perform satisfactorily to purify the blood and have developed a good reputation from extensive, successful use in hospital clinics, it is recognized that expert assistance of hospital technicians is needed in connecting the patient to the artificial kidney and associated assisting machines. An improved artificial kidney is still needed that is more easily handled and more easily attached to the patient and to the machine which assists during dialysis in controlling blood flow, dialysate flow and the like.

It has also been recognized as desireable to make an artificial kidney having a single configuration of size and shape but which provides preselected patient-tailored capabilities of rate of water removal and clearances for urea, creatinine, uric acid and other metabolic wastes.

It is therefore a primary object of the invention to provide a hollow fiber artificial kidney that is less expensive to make and more convenient to use than current commercial hollow fiber artificial kidneys.

Another object of this invention is to provide an automated continuous process for making the improved artificial kidneys of this invention.

A further object of this invention is to provide a new hollow fiber bundle adapted to be bonded in a jacket to form a one-piece, integral, non-disassembleable artificial kidney; a related object is to provide the new bundle and jacket portions of such shape, size and arrangement relative to each other that machine handling and bonding of the parts into a unit on a continuous basis is facilitated and human effort required in manufacture is minimized.

A still further objective is to provide an artificial kidney which integrates into a one-piece, integral construction one or more of the necessary supplementary segments of the extracorporeal circuit which are ordinarily separately provided and used during intermittent dialysis such as, for example, blood tubing, drip chambers, blood filters, infusion sites, blood pump tubing, etc.

Another important object is to provide a hollow fiber artificial kidney which minimizes the surface area of foreign material to which blood is exposed while following in the extracorporeal circuit including gases, particularly air, and thereby minimizes the need for anticoagulant.

SUMMARY OF THE INVENTION

This invention provides hollow fiber artificial kidneys which are new and improved in the respect that they are one-piece, integral, non-disassembleable units. In preferred embodiments, the artificial kidney includes as an integrated part of the one-piece unit, selected optional features which eliminate blood-gas interfaces in the entire extra corporeal circuit and may include drip chambers, blood filters, blood pump elements, dialysate purification elements, and the like.

The method of this invention provides steps and means for continuously making new hollow fiber bundles comprising fibers potted in longitudinally spaced tubesheets, which tubesheets are adapted for bonding to a pair of surrounding jackets to thereby form an integral, non-disassembleable one-piece unit; the resulting one-piece unit comprises a pair of blood chambers spaced apart and separated by an interconnecting dialysate chamber formed by curvilinear portions of the jackets. The fiber bundle and jacket portions are so shaped and arranged that they interfit and can be bonded together and to each other in a continuous manner.

BRIEF DESCRIPTION OF THE DRAWINGS

For a more complete understanding of the new hollow fiber artificial kidney constructions of this invention and the various methods by which they are manufactured, reference is made to the accompanying drawings and to the detailed description which follows:

FIG. 7 is a broken out top view of one end portion of a kidney similar to that shown in FIG. 5.

FIG. 8 is a cross-sectional view of the kidney taken at location of 8—8 in FIG. 5 after bonding of the fiber bundle and jacket portions into a one-piece, integral unit.

FIG. 9 is a cross-sectional view of the kidney taken along 9—9 of FIG. 7.

FIG. 10 is a top view of another preferred embodiment of an artificial kidney of this invention.

FIG. 11 is a top view of yet another modified and preferred embodiment of this invention.

FIG. 13 is a schematic representation of the method of this invention.

FIG. 14 is a perspective view pictorially illustrating the continuous method for making fiber bundle assemblies.

FIG. 15 is a sectional view of one of the end portions of a modified embodiment of this invention; and FIG. 16 is a sectional view of an end portion of another modified embodiment of this invention.

DETAILED DESCRIPTION

Figure 1:
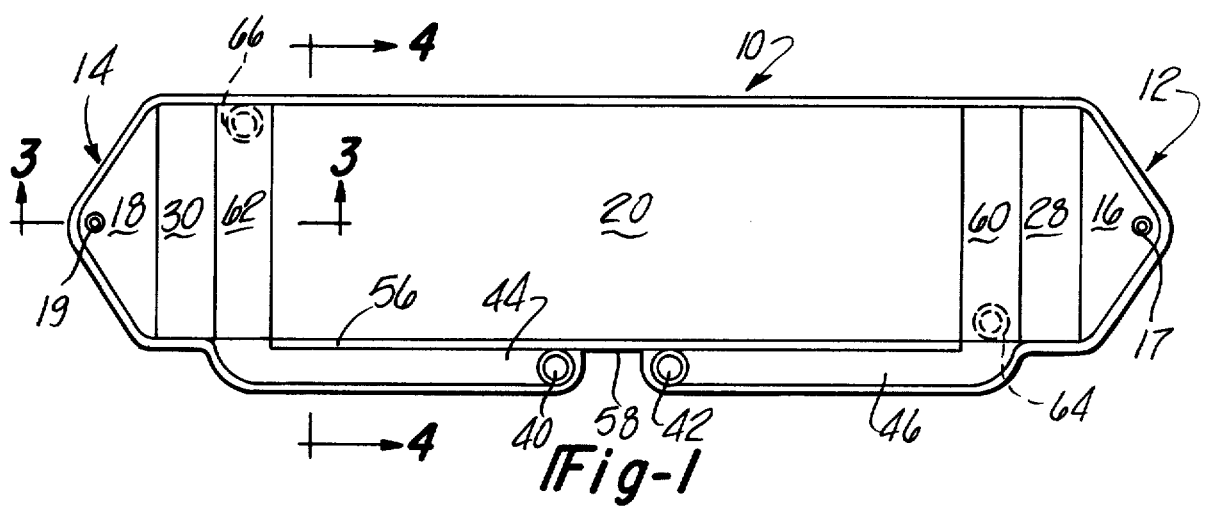
FIG. 1 is a top view of one embodiment of an artifical kidney of this invention.
Figure 2:
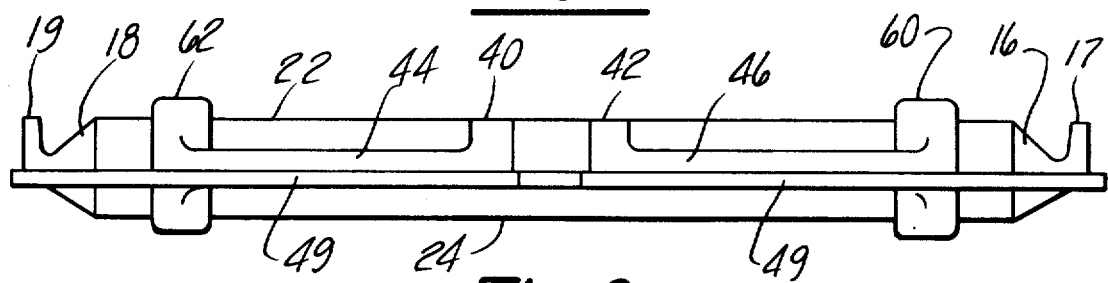
FIG. 2 is a side view of the artificial kidney of FIG. 1.
Figure 3:
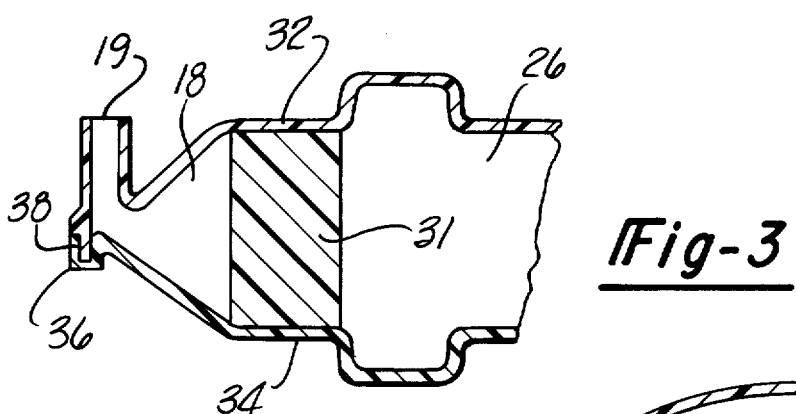
FIG. 3 is a cross-sectional view of the kidney taken along 3—3 in FIG. 1.
Figure 4:
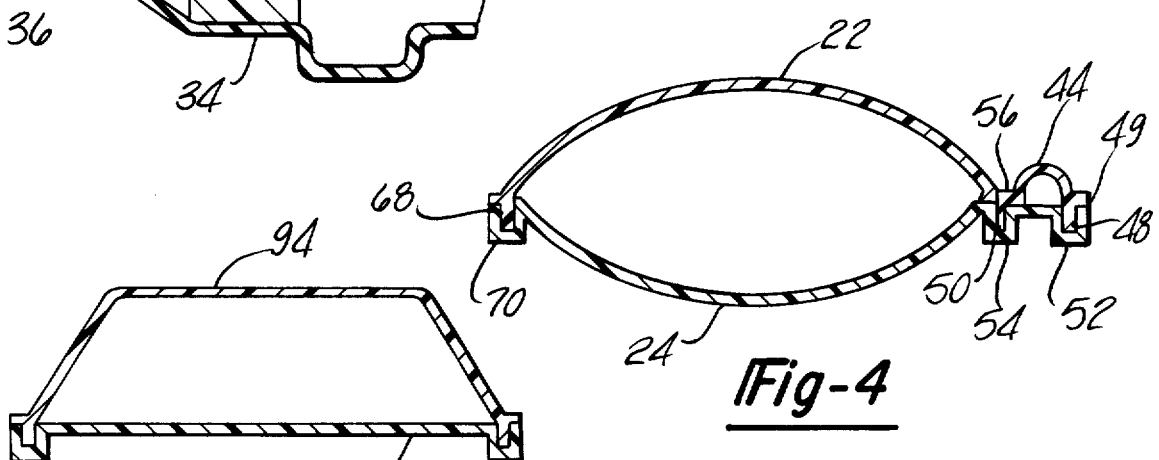
FIG. 4 is a cross-sectional view of the kidney taken along 4—4 in FIG. 1.
Figure 5:
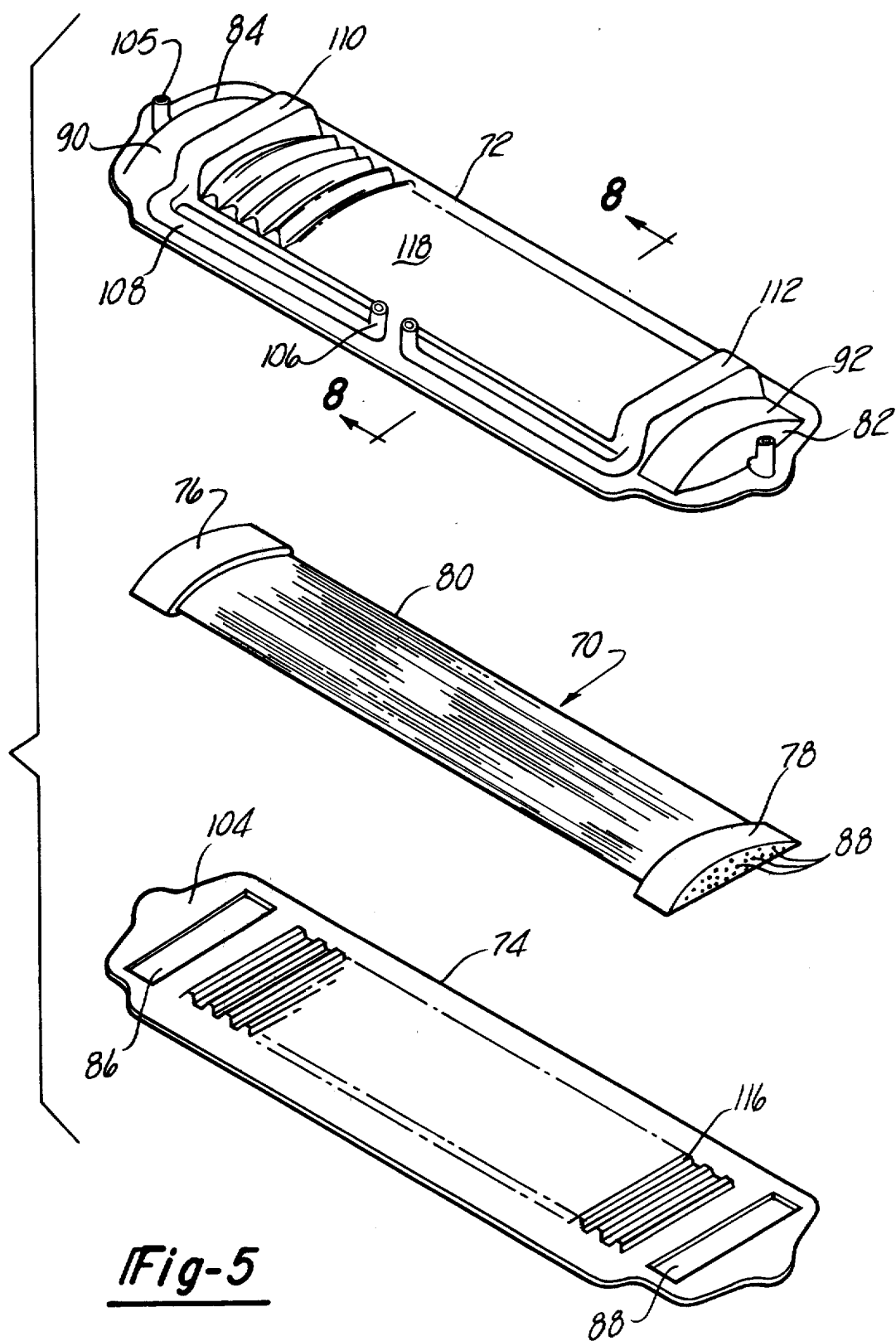
FIG. 5 is an exploded view of a preferred embodiment of an artificial kidney of this invention showing a hollow fiber bundle with longitudinally spaced tubesheets on each end of the fibers positioned between the mating elongate jacket portions which interfit therewith and after bonding form one embodiment of the one-piece, integral artifical kidney of this invention.

Referring to the drawings, the embodiment shown in FIGS. 1-4 and the preferred embodiment shown in FIG. 5 in unassembled component form will be used to explain the first form of the one-piece, integral non-disassembleable construction which characterizes this invention. In FIG. 1, the kidney generally designated 10, comprises end portions generally designated 12, 14 which define, or encompass an inlet blood chamber 16 having an inlet blood port 17 and outlet blood chamber 18 having an outlet blood port 19, respectively. Blood chambers 16 and 18 are spaced apart and interconnected by a dialysate chamber, generally designated 20, which is formed of curvilinear portions 22 and 24. Blood chambers 16 and 18 are blood tight chambers which are sealed from dialysate chamber 20 at tubesheet areas 28 and 30; as seen in FIG. 3, blood chamber 18 is separated from dialysate chamber 20 by tubesheet 31 which supports and encapsulates a multiplicity of hollow fibers 26, the open ends of which are in communication with the interior of blood chamber 18. Tubesheet 31 is bonded in liquid tight sealed relationship with jacket walls 32, 34 which completely enclose tubesheet 31 and are in full surface contact therewith. Wall 32 is, in turn, bonded to wall 34 along the exterior edges of end portion 14 in a tongue and groove joint consisting of a groove portion 36, integral with wall 34, and a tongue portion 38, integral with wall 32. A similar construction is employed to separate blood chamber 16 and dialysate chamber 20 and to seal the mating portions of the jackets together in end portion 12, the details of which are not shown.

Figure 17:
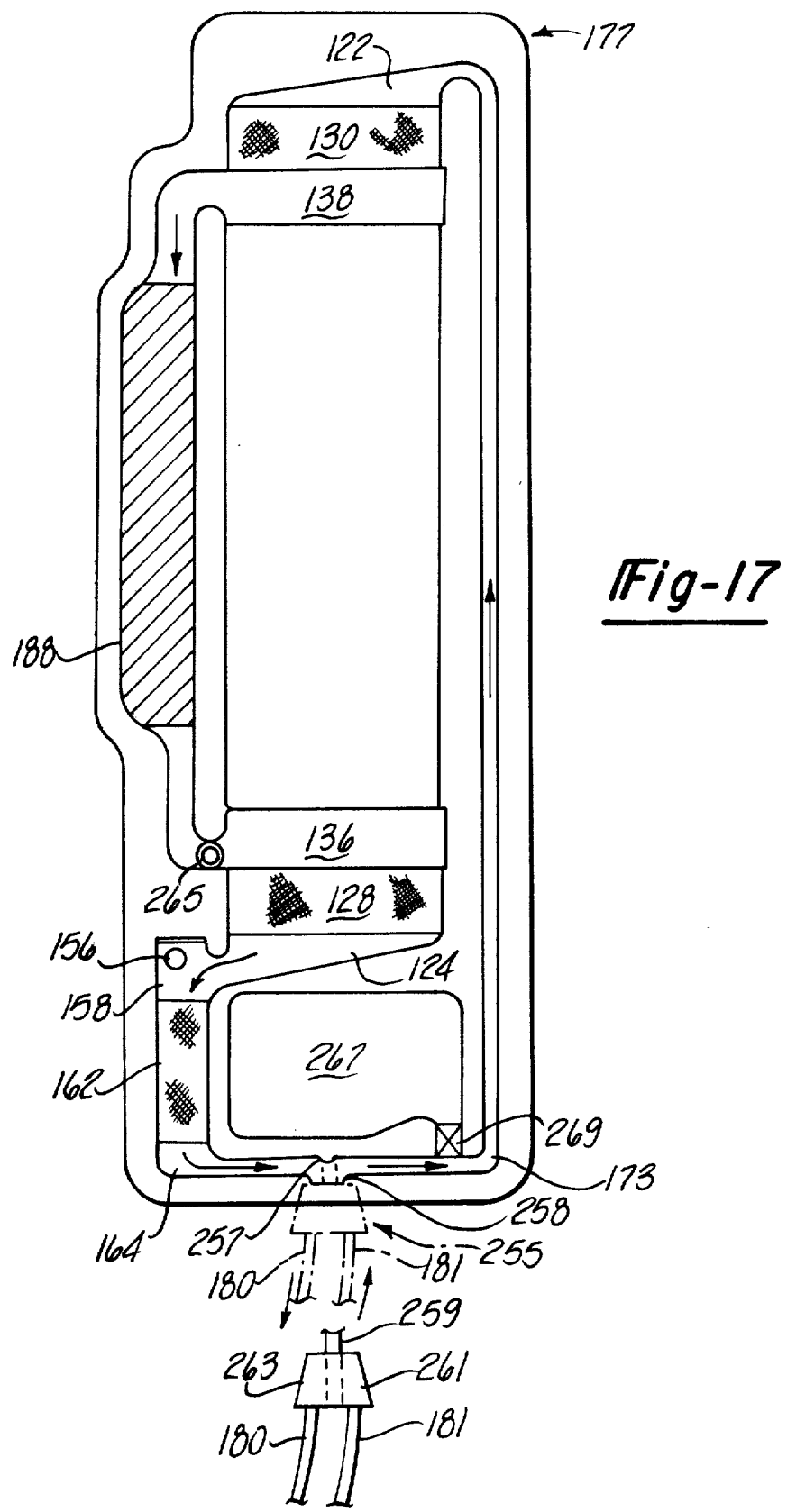
FIG. 17 is a top view of the type of artificial kidney shown in FIG. 11 further modified to illustrate single ports for entry and exit of blood and dialysate and means for flushing blood from the kidney.

Dialysate chamber 20 is provided with an inlet dialysate port 40 and an outlet dialysate port 42, each having an internal construction similar to that shown for blood port 19 in FIG. 3 and as shown in FIG. 8. Dialysate ports 40, 42 are located in dialysate channels 44, 46 respectively. They are integral with curvilinear wall portion 22, terminate in a pair of spaced apart, downwardly extending tongues 48, 50 and are adapted to be received by a pair of spaced, mating groove portions 52, 54 respectively, which groove portions 52, 54 are integral with curvilinear wall portion 24. Bonding occurs between portions 22 and 24 at 49 and along wall portion 56 which separates dialysate channel 44 from curvilinear portion 22. Portion 56 is bonded to the upper surface which defines the inner portion of groove 54 along the full length of contact including the portion designated 58 which lies between the central end portions of dilysate channels 44, 46. Dialysate ports 40, 42 are shown in FIG. 1 in locations adjacent to the middle portion of dialysate chamber 20, but their location is not critical. They may be satisfactorily located at any selected point along the full length of dialysate channels 44, 46 or at any point on the surface of dialysate manifolds 60, 62 as for example at locations on opposite sides of the dialysate chamber as shown in phantom at 64, 66, or may be combined into a single port as shown in FIG. 17.

Bonding of curvilinear portions 22 and 24 on the side of kidney 10 opposite from dialysate channels 44, 46 is effected by sealing tongue 68, integral with portion 22, into receiving groove 70, integral with portion 24, along the entire length of their contact.

The internal arrangement of the hollow fiber bundle in the integral one-piece kidney 10 in relationship to the surrounding bonded elongate jacket portions is most easily seen by referring to the separated component parts in FIG. 5. In FIG. 5, fiber bundle 70 is shown separated from mating elongate jacket portions 72 and 74 which are adapted to receive, nest with and bond to contiguous portions of fiber bundle 70. Fiber bundle 70 consists of a pair of spaced apart tubesheets 76, 78 and a multiplicity of hollow fibers 80. Hollow fibers 80 are capillary man-made fibers having a small diameter and thin wall thickness which are semi-permeable, or porous, and capable of separating from blood flowing therein urea and other metabolic wastes and passing those wastes through the wall into a dialysate fluid flowing outside the fiber in the dialysate chamber. The open ends of fibers 80 terminate in the outer end surfaces of tubesheets 76, 78 and provide communication between the interiors of blood chambers 82, 84 after jacket portions 72, 74 have been bonded to tubesheets 76, 78 and to each other along the entire peripheral end and side mating portions thereof. It is apparent that areas 86, 88 in jacket portion 74 have substantially the same shape and size as the lower half of mating tubesheets 76, 78, respectively. It may also be seen that jacket portion 72 is provided with similarly shaped tubesheet receiving depressions 90, 92 such that it is necessary only to nest fiber bundle 70 in contact with jacket portions 72, 74 and bond all contiguous surfaces together to form a one-piece integral kidney having the preferred configuration and shape of the component parts shown in FIG. 5.

Figure 6:
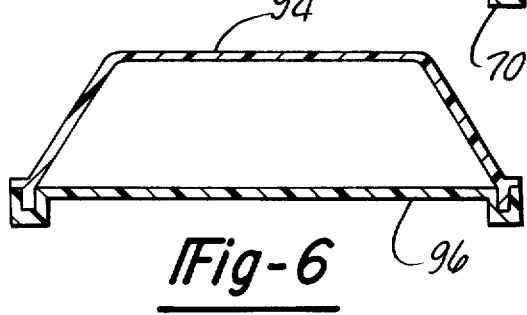
FIG. 6 is a cross-sectional, similar to the view shown in FIG. 4, illustrating a modified cross-sectional shape of the dialysate chamber.

Fiber bundle 70 is a key component of the one-piece integral kidney of this invention. Fibers 80 are arranged linearly so as to substantially fill the lenticular cross-sectional area of the preferred embodiment as shown in FIG. 8, or the equivalent cross-sectional areas of the embodiments shown in FIGS. 4 and 6. It is to be understood that the curvilinear portions 22 and 24 which define the dialysate chamber 20 in the embodiment of FIGS. 1-4 are preferred because of greater ease of manufacture but are functionally equivalent to the straighter wall portions 94, 96 which are illustrated in FIG. 6 or to cross-sectional areas which are less lenticular, up to and including circular. Similar bonding and sealing elements and procedures may be used with the modification shown in FIG. 6 as those described above in connection with FIG. 4. One of the advantageous aspects which accrues from the depicted shape of tubesheets 76, 78 is that such a shape enables the use of bonding techniques and equipment in continuous assembly line methods of production, which will be further explained hereinafter in connection with the method of this invention. Another advantage of fiber bundle 70 is that continuous strands, consisting of a multiplicity of fibers, can be potted or encapsulated into a tubesheet at spaced locations along a line of continuously, or intermittently, advancing fibers and severing through the tubesheets to form fiber bundles 70. This procedure eliminates the necessity for centrifugal potting by the method of Geary U.S. Pat. No. 3,442,002, and is described in further detail in the portion of this specification which explains the method of this invention.

It is satisfactory to use any of the known semi-permeable hollow fibers that are capable of functioning as a dialysis membrane, such as, for example, cellulose esters, cellulose, polyamides, polyesters, styrene polymers, etc. as taught in U.S. Pat. Nos. 3,228,876, 3,228,877, 3,423,491, and 3,532,527.

The embodiment of the invention shown in FIGS. 5 and 7-9 represents the best mode of the invention primarily because of the ease with which it may be manufactured; that embodiment includes features which include strengthening elements in the dialysate chamber portion and a dialysate manifold design to insure commercial utility of the kidney under current and contemplated use conditions. These features of this preferred embodiment will now be explained.

Referring to FIGS. 7-9, it will be seen in FIG. 7 that tubesheet 76 and the overlying portion 90 of jacket portion 72 are in surface contact and are sealed together as along break away line 100. As explained in greater detail in the description of the method, tubesheet 76 and jacket portions 90 and 86 which are preferably fabricated from thermoplastic polymeric compositions are bonded together by heating and pressure sealing the mating surfaces into an integral, non-disassembleable form. Optionally, however, the seal between tubesheet 76 and mating jacket portions 86, 90 may be supplemented by the inclusion of an elastic gasket or O-ring, or other sealing-assist means.

Jacket portion 90 extends beyond the outer end face 102 of tubesheet 76 to form, with the mating inner-surface 104 of jacket portion 74, blood chamber 84. Outlet blood port 105 is positioned adjacent the outer wall of blood chamber 84 and is adapted to receive a conventional fitting on the venous blood line return to the patient. Fibers 80 extend into and through tubesheet 76 and their open ends terminate in the plane of face 102 within blood chamber 84.

During dialysis the outer surfaces of fibers 80 are bathed in the constantly flowing dialysate which enters through inlet dialysate port 106, flows through dialysate channel 108 in the direction of the arrow seen in FIG. 7, into dialysate manifold 110. Dialysate manifold 110 is sized so as to provide uniform dialysate flow over all of the fibers 80 in chamber 72 from side to side and throughout its length. Although the optimum size of dialysate manifold 110 will vary, it has been found to be desirable to size manifold 110 such that the pressure drop across the manifold is a small fraction of the pressure drop over the length of the fibers, that is, from dialysate inlet header 110 to the dialysate outlet header 112; preferably the pressure drop across inlet header 110 is less than about ten percent of the total pressure drop across the fibers from end to end.

In dialysis, it is customary to vary the pressure on the dialysate in order to obtain the needed pressure differential, transmembrane pressure, across the semi-permeable wall of the hollow fiber for the control of the rate of water removal from the blood during dialysis. Under conditions periodically encountered, the dialysate negative pressure reaches as high as about −500 millimeters of mercury or approximately minus 10 pounds per square inch, both relative to atmospheric pressure, although routine dialysis pressures ordinarily are sustantially lower and in the range of about minus 2 to about minus 6 psi. For an elongate, lenticular shaped construction as shown in FIGS. 5 and 7-9 inclusive, the dialysate chamber can be reinforced against collapse at high negative pressures by a plurality of transverse ribs 114 in jacket portion 72 and another series of transverse ribs 116 in jacket portion 74. As shown ribs 114, 116 extend the full length of dialysate chamber 118 but it will be understood by those skilled in this art that this number of ribs, their depth and shape should be varied to provide the required resistance to collapse when the length and shape of the curvilinear dialysate chamber and the thickness and strength of the jacket material being employed are appropriately taken into account.

FIGS. 10, 11 and 17 illustrate modified forms of the type of elongate, one-piece, integral construction shown in the preferred embodiment in FIGS. 5 and 7-9. These modified forms illustrate, in general, the flexibility of final kidney design which accrues from the use of the fiber bundle and mating jacket portions approach to the fabrication of artificial kidneys. Basically, by enlarging the jacket portions contiguous to the dialysate chamber and modifying their configuration, optionally selected supplementary segments of the extracorporeal circuit are are easily incorporated and become integral components in the one-piece constructions which characterize this invention, and their integration into the unit merely requires an additional step in the basically unchanged assembly line process of making unmodified constructions.

Referring to FIG. 10, a further improved kidney, generally designated 120, is shown having an inlet blood chamber 122 fed through inlet blood port 145 and an outlet blood chamber 124, separated and interconnected by an intervening dialysate chamber 126. Tubesheets 128, 130 support hollow fibers, not shown, which extend through dialysate chamber 126 as above described. Dialysate enters through dialysate port 132, flows upwardly through integral dialysate channel 134 into dialysate manifold 136, thence over the fibers to outlet manifold 138, integral dialysate outlet channel 140 and outlet port 142.

Since the blood chambers are formed when the jacket portions are sealed together, it is possible to form a blood flow conduit connected to a blood flow chamber in the same manner and add elements to this blood flow conduit which can be used to carry out functions previously assigned to separate components or perform functions previously not incorporated into hemodialysis circuitry. A good example is the drip chamber used in current blood tubing sets to carry out several functions during dialysis. These functions are shown to be incorporated into the kidney construction as a bubble collection chamber 158 which is connected to the blood outlet chamber 124 and a serum cap port 156. Port 156 is provided as a site for injections and sample withdrawal. A hydrophobic membrane 157 is mounted to form the top surface of chamber 158 and provides as-needed venting to atmosphere of collected air bubbles in the blood without permitting blood, or other liquid, to pass through the membrane which may be microporous or equivalent. This construction eliminates the air-blood interface which normally exists in conventional hemodialysis drip chambers and provides an extracorporeal blood circuit free of any blood-gas interface. Integrally mounted blood filter 162 is located in the bubble collection chamber 158.

The venous blood channel 164 below the bubble collection chamber is shown to be utilized for sites for bubble detection means 166; non-invasive venous blood pressure measurement means 168; positive blood pressure control means 170; and analytical measurement means 172 for analysis of concentrations of solutes such as urea, creatinine, and uric acid and optionally including pH. Blood inlet channel 173, also includes a site for electrodes 174 which extend into the blood flow channel 150 to measure pH and metabolic waste concentrations. A heparin and/or saline infusion site 175 is also provided in the blood inlet channel 173.

Integrally mounted in dialysate outlet channel 140, analytical means 176 is provided to enable analytical determinations which can be made in the dialysate as a means of determining patient solute levels and kidney performance. Blood leak detection means 178 is also located in dialysate outlet channel 140. Through incorporation of circuit components into the disposable dialyzer, the blood lines 180, 181 beyond blood ports 145 and 179, respectively, can be simplified and shortened to the extent that they are integrated into the one-piece construction. Sites on the simplified blood line are provided for a blood pumping means 182 and for a blood flow rate measuring means 184.

FIG. 11 shows a further modified kidney construction of this invention generally designated 177, which integrates into a one-piece integral construction additional extracorporeal circuit segments to those included in the kidney shown in FIG. 10. Actually, FIG. 11 provides practically all of the important supplemental segments of the extracorporeal circuit that are necessary other than the blood access means and dialysate supply and monitoring means. In addition to the supplemental segments which are functionally the same as those on the kidney of FIG. 10, for which like numbers have been used even though the segment is differently located, the kidney of FIG. 11 includes integrally mounted pump 186 of, for example, the roller compression or bellows type or the centrifugal impeller type in the blood inlet channel and a dialysate purification, or sorbent, pack 188. From blood pump 186, the inlet blood channel transports arterial blood to the top of kidney 177, and it moves downwardly and exits adjacent to the blood inlet where it initially entered kidney 177. Sorbent pack 188 is integrally mounted to receive spent dialysate from dialysate manifold 138 and absorbs, or otherwise removes urea and other metabolic wastes from the dialysate and readies same for recirculation to dialysate inlet port 132. Pressure transducer connection means 160 communicates with the interior of the bubble collection chamber adjacent to part 156 for measurement of blood pressure at the outlet end of the kidney 177.

Figure 12:
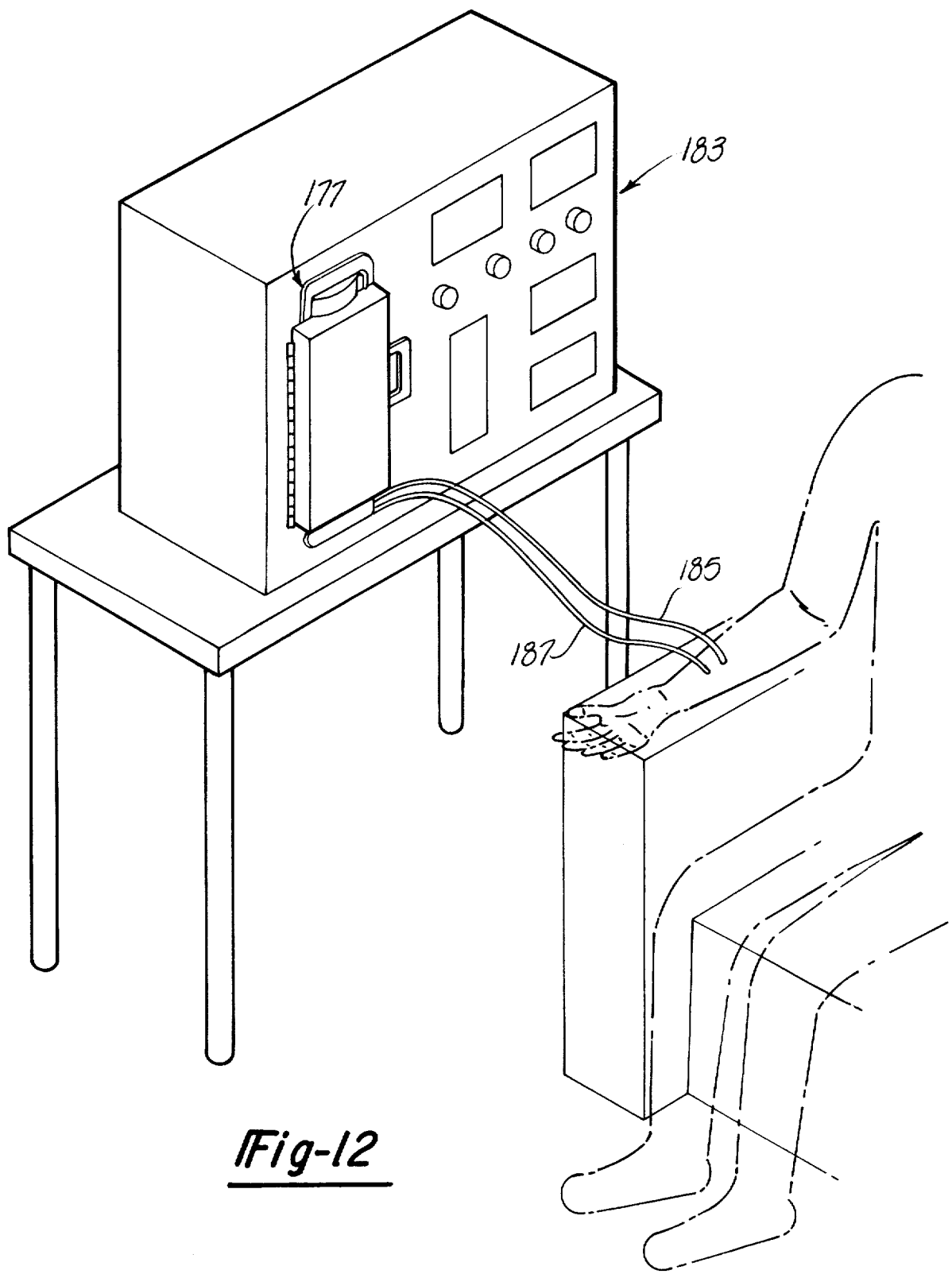
FIG. 12 is a perspective view illustrating the kidney embodiment of FIG. 11 in position on a dialysate supply and control machine.

The kidney embodiment of FIG. 11 is pictorially shown in position for use in hemodialysis in FIG. 12. Kidney 177 is directly attached to suitable supports, not shown, on the front face of the dialysate delivery machine generally designated 183, and to the patient by relatively short arterial and venous blood lines 185, 187 which are attached to inlet blood port 145 and outlet blood port 179, respectively. Dialysate lines are eliminated by virtue of direct connection of dialysate inlet port 132 and outlet port 142 with dialysate supply and re-circulation channels or conduits located inside dialysate delivery machine 183.

The kidney 177 of FIG. 11 is shown in FIG. 17 wherein it is further modified to illustrate single ports for the entry and exit of blood and dialysate; it also includes integral means for flushing blood from the kidney to the patient and preparing the kidney for possible reuse in a sterile manner. As may be seen in FIG. 17, wherein the previously used numbers are again used for similarly functioning segments, a single port generally designated 255, is provided for the entry and exit of blood in lieu of separate entry port 145 and exit port 179 as shown in the embodiment of FIG. 11. Blood port 255 is located at the juncture of blood inlet channel 173 and blood exit channel 164 and includes an inner wall projection 257 and an outer wall projection 258. A connector 256 is frusto-conically shaped to abut against projection 258 and connect blood supply line 181 and blood return line 180 into common port 255. Connector 256 is interiorly divided into two compartments 261, 263 by septum member 259 which projects from the inner sealing surface of connector 256 sufficiently to abut and seal against projection 257 when connector 256 is inserted in port 255 to thereby interconnect inlet blood line 181 with channel 173 and outlet blood line with channel 164.

Dialysate is introduced into manifold 136 and removed from sorbent pack 188 through a single dialysate port 265 which employs similar elements and closure means to those used at blood port 255, the details of which are not illustrated in FIG. 17.

In addition to the manufacturing simplication which results from the single port construction, the kidney of FIG. 17 is also easier for the patient, or assisting technician, to connect in preparation for dialysis. In the normal sequence of preparing a hollow fiber kidney for use, after flushing, the kidney must be primed with blood after physical endwise inversion of the kidney from the position the kidney normally has during dialysis in order to allow any entrapped gas to vent to atmosphere. Common blood port 255 eliminates the necessity for physically inverting the kidney in order to cause blood priming through the kidney in an upward flow path because this may be accomplished by withdrawing connector 256, rotating it 180° and reconnecting it in blood port 255 to thereby reverse the blood line connections. Similar reversal is available at dialysate port 265 when needed for back flushing, or the like.

At the end of a hemodialysis treatment it is customary to flush the patient's blood in the artifical kidney backwardly through the kidney and the blood lines into the patient; this step normally requires technician assistance to disconnect the arterial blood line, connect a source of sterile saline and carefully displace the blood without injecting saline solution into the patient. The construction of FIG. 17 includes means for automatically backflushing blood from the kidney and associated segments with approximately the predetermined required quantity of sterile saline to displace the blood in the extra corporeal circuit thereby simplifying the procedure, while concurrently preparing the kidney for reuse, particularly reuse by the same patient. Sterile saline pouch 267, having a flexible, upwardly extending dome-shaped upper layer is preliminarily filled with the precalculated quantity of sterile saline solution substantially equal to the volume of blood in the artifical kidney associated segments and blood lines to the arterial blood access. This solution is isolated from inlet blood channel 173 by valve 269 until back flushing is desired; at such time with the blood pump off valve 269 is opened and compressive force is applied, for example by means associated with delivery machine 183, to expel the sterile saline from pouch 267.

DETAILED DESCRIPTION OF THE METHOD

Broadly stated, the method of this invention is of the assembly line type in which a hollow fiber bundle with tubesheets attached to the fibers as end members is formed and positioned between two jacket members which are separately formed to surround and sealingly mate with the fiber bundle. In the preferred method, the jacket members are so configured as to form a pair of fluid-tight end chambers spaced apart by an intervening fluid-tight chamber; the intervening chamber internally contains the fiber bundle. These three chambers are simultaneously formed by joining the jacket members to the tubesheet portions of the fiber bundle and to each other on all contacting, mating surfaces. The resulting device is the one-piece, integral non-disassembleable device of this invention. It is to be understood that the inventive features of the method of this invention are not confined to the manufacture of the constructions shown in FIG. 1-12 which are especially well suited for hemodialysis and that those constructions are illustrative only; the constructions of this invention are intended to include devices suitable for use in all fluid separation processes which employ hollow, semipermeable fibers as a membrane for separating components or solutes from a fluid including, for example, ultrafiltration, reverse osmosis, and industrial dialysis in addition to the heretofore described hemodialysis devices. Certain of these devices have a single port in the fiber bundle-containing chamber, and the method of this invention is equally applicable to the manufacture of such one-piece integral devices.

As schematically illustrated in FIG. 13, the process of this invention comprises the steps of advancing strands of hollow fibers along a line, and consolidating a plurality of strands into a tow. At a first location on the tow the fibers are potted, or encapsulated with a suitable polymeric composition to form a tubesheet. The tow is advanced a distance equal to the desired length of the fiber bundle and a second tubesheet is formed. After a further advance of the tow, the tubesheets are trimmed and transversely severed through the tubesheet and the fibers therein to form a hollow fiber bundle assembly 190. Jacket portions 191, preferably two in number, are separately formed to the required size and configuration to sealingly mate with the tubesheets of the fiber bundle, such as the configurations illustrated in FIGS. 1-12. A fiber bundle assembly 190 is then positioned between the jacket portions 191 in the assembly operation, and supplemental segments are added, if desired, such as one or more of the features illustrated in FIGS. 10, 11 and 17; the assembled components are then bonded or sealed together at all contact surfaces. These steps are suitable to produce a wide range of one-piece, integral, non-disassembleable fluid separation devices that are infinitely variable as to size, configuration and the like and may be easily modified to accommodate specific jackets and fiber bundles which are optimally suited for the specifically contemplated fluid separation end use.

The process is also variable with respect to the assembly of the fiber bundle. For example, the tow may include hollow fibers of different types, made from different polymeric compositions having different degrees of permeability for low middle and high molecular weight solutes, and varying capacities to separate water from blood, or other aqueous liquid flowing within the fibers. Similarly, the tubesheet size and shape is easily changed merely by alteration of the shape of the cavity in the mold to accommodate varying sized tows; fiber bundles of any desired length may be made by varying the distance between tubesheets on the tow and thus the total quantity of semi-permeable surface area available for use is easily changed, as desired.

The tubesheets are formed by filling the interstices between the linearly arranged hollow fibers in the tow, while clamped within the mold, and filling the mold itself with a liquid polymeric composition which is solidified in the mold to form a tubesheet having the external shape of the cavity in the mold. Polymeric compositions known generally as hot melt adhesives, which are widely used in the packaging industry, are suitable for use in making tubesheets. More specifically low molecular weight polyethylene resins of the type described in U.S. Pat. Nos. 3,428,591 and 3,440,194 have been found to be satisfactory. The tubesheets are formed of such length along the fiber axes in the tow as to permit the subsequent cutting through the tubesheet and fibers therein in the central portion of the formed tubesheet to form two tubesheets. The formed tubesheet is thus at least twice as long as the axial, or longitudinal length, of the tubesheet that is desired on the fiber bundle assembly being made. An advantageous method of potting hollow fibers in a tow to form tubesheets specially adapted to accommodate division into two adjacent tubesheets by cutting while concurrently providing a planar tubesheet face substantially flat and free of surface imperfections or voids is disclosed in copending application Ser. No. 805,602, filed June 10, 1977, as the invention of Alfred R. Tigner, entitled "Method For Forming Tubesheets on Hollow Fiber Tows And Forming Hollow Fiber Bundle Assemblies Containing Same" and which is owned by the assignee of this application.

The process of forming fiber bundles in accordance with the method of this invention is more specifically illustrated in FIG. 14. As shown in FIG. 14, hollow fibers in a plurality of continuous strands 192, each strand containing a plurality of fibers, e.g., 30 to 600 and preferably about 200 to 600 are collected, or brought together around rotatable drums 194, 196, 198 to form a tow 200. Tow 200 typically may contain between about 3000 and 30,000 hollow fibers; for use in an artificial kidney each hollow fiber is of capilliary size and typically is in the range of about 150 to about 300 microns internal diameter and has a wall thickness in the range of about 20–50 microns.

After tow 200 is formed it is advanced to a tubesheet forming station generally designated 202. At station 202 tow 200 is positioned in a two piece potting mold. The lower section of the mold consists of a heated portion 204 located between contiguous cooling and tow clamping portions 206, 208. The upper section consists of a corresponding heated portion 210 flanked by cooling and tow clamping portions 212, 214. Tow 200 is secured between heated mold portions 204 and 210 by the clamping surfaces 209, 211 of tow clamping portions 214 and 212, respectively, which surfaces bear against the tow when the upper section of the mold is brought into pressure contact with the lower section by conventional means, not shown. After the mold is closed, the selected liquid polymeric tubesheet composition is flowed into the mold through resin supply line 213, and through the interstices between the hollow fibers within the heated mold portions 204, 210 and the excess resin flows outwardly through resin outlet line 215. Typically, the tubesheet resin is a hot melt adhesive which is solid at ordinary room temperature and at temperatures of 65° C. to 110° C. becomes a liquid with a low viscosity in the range of about 500 to 5000 centiposes at the potting temperature of about 100° C.–170° C. Low viscosity resins tend to completely wet and encapsulate the hollow fibers in shorter times and are therefore preferred. After the resin is introduced to fill the interstices between the fibers and the mold which requires about 30 seconds to about 20 minutes at flow rates of 10 to 100 grams per minute at 100° C. to 170° C. depending upon resin viscosity, resin flow is terminated and the mold is cooled to solidify the resin and form the tubesheet, 216. After cooling the mold is opened and the tubesheet is removed. While it is preferred to employ thermoplastic polymeric compositions for making tubesheets, it is also satisfactory to employ thermosetting polymeric compositions, such for example as phenolics, polyurethanenes, epoxy resins, etc. As will be apparent to those skilled in the polymeric resin art, use of thermosetting resins requires appropriate changes in the mold 202 to accommodate the specific thermosetting resin which is selected.

After tubesheet 216 is removed from mold 202 tow 200 is advanced the distance desired for the succeeding fiber bundle assembly, usually about 15 to 40 centimeters, and for artificial kidneys preferably about 20 to 35 centimeters. As a guide, a 33 centimeter tow containing about 7200 fibers having a wall thickness of about 20 to 40 microns and an internal diameter of about 200 microns produces an artificial kidney having about 1.5 square meters of permeate surface area. Slitting or cutting tubesheet 216 is effected by conventional procedures which usually include cutting and then trimming to provide the necessary smooth, particle and void free tubesheet surface for blood contact within a blood chamber. As illustrated in FIG. 14, a tubesheet such as 216 is advanced to the location of power driven cutter 218 and final tubesheet trimmer 220 which is operated by suitable means such as cylinder 222. Cutting through tubesheet 216 in the central portion along line 224 creates a pair of tubesheets 226, 228, each of which encapsulates approximately half of the hollow fibers within formed tubesheet 216 and becomes the end member of a fiber bundle assembly 190. It will be apparent that a plurality of molds 202 may be positioned along tow 200 for simultaneous tubesheet formation to thereby increase the rate of production, and that FIG. 14 is illustrative only.

Jacket 191, which may have configurations such as those shown in FIGS. 1–5 may be fabricated from a wide variety of suitable plastics. The selected plastic is preferably substantially trnsparent and should be impact resistant, and sufficiently strong in thin sections to withstand collapse under the internal pressures or rupture under positive pressures customarily used in the dialysate chamber, as above described; the plastic must be capable of deformation into the desired shape by conventional procedures such as injection molding or thermoforming and should be easily joinable or sealable to itself, preferably by heat sealing at reasonably low temperatures by the application of pressure. Suitable materials include polypropylene, impact polystyrene, and acrylonitrile-butadiene-styrene resins. Enhancement of easy sealing is obtained by providing a lower melting point plastic layer on the mating surfaces of the polypropylene, ABS, etc. such as polyethylene. Such laminates may be formed by conventional laminating procedures with, or without, the use of supplemental adhesives.

The preferred process of this invention employs jacket portions configured to encompass spaced apart blood chambers and an interconnecting dialysate chamber of the type shown in FIGS. 5 and 7–9 inclusive. It is to be understood however that the basic objective of providing a one-piece, integral non-dissembleable hollow fiber device may be accomplished by variations which do not employ jacket portions that are identically configured and yet such constructions, after assembly are functionally equivalent to the preferred devices of this invention. Two such examples are illustrated in FIGS. 15 and 16. In FIG. 15, jacket portion 230 and mating jacket portion 232 terminate in end portions 233 and 234 respectively which overlie and are sealed to the outer surface of tubesheet 236 over a portion, or all, of the axial outer surface of tubesheet 236. A blood chamber 238 is defined by separately formed blood header wall member 240 which may consist of one or more parts. Member 240 overlies a portion of the outer surface of tubesheet 236 and overlaps a portion of the outer end jacket walls 232 and 234. The sealing of jackets 230, 232 to tubesheet 236 may be effected in a prior separate step, or equally effectively may be accomplished concurrently with the sealing of header wall 240 to both the tubesheet and jacket wall members.

In FIG. 16, tubesheet 242 is sealed to blood header and wall portions 244, 246 which overlie the entire axial outer surface thereof. Jacket portions 248, 250 terminate in end portions 252 and 254, respectively, and these portions overlie and are sealed to header walls 244 and 246, respectively. The tubesheet-blood header mating portions may be pre-assembled and sealed together as a unit prior to, or simultaneously with the sealing of the jacket portions thereto.

It is believed to be apparent that novel and improved onepiece integral hollow fiber artificial kidney constructions, and novel improved methods of fabricating such artificial kidneys and other hollow fiber separatory devices have been described and provided in accordance with the above stated objects of the invention. The artificial kidney constructions which are shown in the drawings and specifically described in this specification are illustrative only; they are, however, especially adapted and well suited to automatically enable the performance of the improved intermittent hemodialysis process described in greater detail in copending application Ser. No. 805,600, filed June 10, 1977, the disclosure of which is hereby referred to for the purpose of supplementing and clarifying the functions of certain of the constructions described herein, particularly those of FIGS. 10, 11 and 17.

What we claim is:

1. An improved hollow fiber artificial kidney comprising in a one-piece integral construction a jacket member having
   (1) spaced apart end portions interconnected by curvilinear portions, said curvilinear portions having portions integral with an exterior surface thereof and at least one of said exterior surface portions extending outwardly from said curvilinear portions for at least a part of the length thereof, said curvilinear portions and said end portions encompassing an inlet blood chamber, a dialysate chamber and an outlet blood chamber, each said chamber being fluid-tight and separated from each other,
   (2) a first tubesheet adjacent one end of said curvilinear portions separating said inlet blood chamber from said dialysate chamber,
   (3) a second tubesheet adjacent the other end of said curvilinear portions separating said dialysate chamber from said outlet blood chamber,
   (4) a multiplicity of hollow fibers embedded in each said first and second tubesheet and extending therebetween, said hollow fibers being semipermeable and the ends of said fibers being open and terminating substantially in the plane of the outer end surface of each said tubesheet thereby providing communications between the interiors of said blood chambers through the passageways in said fibers, said hollow fibers between said tubesheets being within said dialysate chamber,
   (5) blood supply means including an integral blood port in communication with said inlet blood chamber for supplying blood thereto,
   (6) blood return means including an integral blood port in communication with said outlet blood chamber for removing blood therefrom, and
   (7) dialysate means including integral inlet and outlet ports in communication with said dialysate chamber for supplying fresh dialysate to and removing spent dialysate from said dialysate chamber.

2. An improved artificial kidney in accordance with claim 1 wherein at least a portion of said blood supply means consists of integral channel means located in at least one of said exterior surface portions of said jacket member.

3. An improved artificial kidney in accordance with claim 2 wherein at least one of said exterior surface (end and said side) portions is substantially flat.

4. An improved artificial kidney in accordance with claim 1 wherein said blood supply means includes associated means integral with said exterior surface portion for effecting at least one function selected from the functions of
   assisting blood flow within said blood supply means, measuring the pressure, temperature and rate of flow of blood therein,
   removing gases from said blood,
   sampling at least one of the whole blood and the fluid portion of said blood therein,
   analyzing and establishing components and acidity of blood therein,
   adding materials to blood therein, and for flushing blood from said blood supply means, said artificial kidney and said blood return means.

5. An improved artificial kidney in accordance with claim 4 wherein said blood return means includes associated means integral with said outwardly extending exterior surface portion for effecting at least one function selected from the functions of
   detecting bubbles in the blood therein, collecting bubbles in the blood therein, removing bubbles from the blood therein, filtering the blood therein, measuring the pressure, temperature and rate of flow of blood therein, sampling at least one of the whole blood and the fluid portion of said blood therein, analyzing and establishing components and acidity of blood therein, and controlling the pressure of blood therein.

6. An improved artificial kidney in accordance with claim 4 wherein said dialysate means includes associated means integral with said outwardly extending exterior surface portion for effecting at least one function selected from the functions of
   detecting blood in said spent diasylate,
   analyzing and establishing the components and acidity of dialysate therein, restoring said component concentrations to approximately the concentration of each said component in said fresh dialysate,
   restoring said acidity to approximately its initial value, and removing metabolic wastes from said spent dialysate.

7. An improved artificial kidney in accordance with claim 1 wherein at least a portion of said blood return means consists of integral channel means located in at least one of said exterior surface portions of said jacket member.

8. An improved artificial kidney in accordance with claim 7 wherein at least one of said exterior surface portions is substantially flat.

9. An improved artificial kidney in accordance with claim 1 wherein said blood return means includes associated means integral with said outwardly extending exterior surface portion for effecting at least one function selected from the functions of
   detecting bubbles in the blood therein,
   collecting bubbles in the blood therein,
   removing bubbles from the blood therein,
   filtering the blood therein,
   measuring the pressure, temperature, and rate of flow of blood therein,
   sampling at least one of the whole blood and the fluid portion of said blood therein,
   analyzing and establishing components and acidity of blood therein, and
   controlling the pressure of blood therein.

10. An improved artificial kidney in accordance with claim 9 wherein said dialysate means includes associated means integral with said outwardly extending exterior surface portion for effecting at least one function selected from the functions of
    detecting blood in said spent dialysate,
    analyzing and establishing the components and acidity of dialysate therein, restoring said component concentrations to approximately the concentration of each said component in said fresh dialysate, restoring said acidity to approximately its initial value, and removing metabolic wastes from said spent dialysate.

11. An improved artificial kidney in accordance with claim 1 wherein at least a portion of said dialysate means consists of dialysate channel means located in at least one of said exterior surface portions of said jacket members.

12. An improved artificial kidney in accordance with claim 11 wherein at least one of said exterior surface portions is substantially flat.

13. An improved artificial kidney in accordance with claim 1 wherein said dialysate means includes associated means integral with said outwardly extending exterior surface portion for effecting at least one function selected from the functions of detecting blood in said spent dialysate, analyzing and establishing the components and acidity of said spent dialysate therein, restoring said component concentrations to approximately the concentration of each said component in said fresh dialysate, restoring said acidity to approximately its initial value, and removing metabolic wastes from said spent dialysate.

14. An improved artificial kidney comprising in a one-piece integral construction a jacket member having (1) end portions spaced apart and interconnected by curvilinear portions, said curvilinear portions and said end portions encompassing an inlet blood chamber, a dialysate chamber and an outlet blood chamber, each said chamber being fluid-tight and separated from each other, and at least one portion extending outwardly from an exterior surface of said curvilinear portions, (2) a first tubesheet adjacent one end of said curvilinear portions separating said inlet blood chamber from said dialysate chamber.

(3) a second tubesheet adjacent the other end of said curvilinear portions separating said dialysate chamber from said outlet blood chamber, (4) a multiplicity of hollow fibers embedded in each said first and second tubesheet and extending therebetween, said hollow fibers having a degree of porosity and the ends of each said fiber being open and terminating substantially in the plane of the outer end surface of each said tubesheet thereby providing communication between the interiors of said blood chambers through the passageways in said fibers, said hollow fibers between said tubesheets being within said dialysate chamber, (5) blood supply means associated with said inlet blood chamber for supplying blood thereto, said blood supply means including associated means integral with said jacket member for effecting at least one function selected from the functions of assisting blood flow within said blood supply means, measuring the pressure, temperature and rate of fluid motion of said blood therein, removing gases from said blood, sampling at least one of the whole blood and the fluid portion of said blood therein, analyzing and establishing components and acidity of blood therein, adding materials to blood therein, and for flushing blood from said blood supply means, and artificial kidney and said blood return means, (6) blood return means associated with said outlet blood chamber for removing blood therefrom, said blood return means including associated means integral with said jacket member for effecting at least one function selected from the functions of detecting bubbles in the blood therein, collecting bubbles in the blood therein, removing bubbles from the blood therein, filtering the blood therein, measuring the pressure, temperature and rate of flow of blood therein, sampling at least one of the whole blood and the fluid portion of said blood therein, analyzing and establishing components and acidity of blood therein, and controlling the pressure of blood therein, and (7) dialysate means associated with said dialysate chamber for supplying dialysate fluid to and removing dialysate from said dialysate chamber.

15. An artificial kidney in accordance with claim 14 wherein said dialysate means includes associated means integral with said jacket member for effecting at least one function selected from the functions of detecting blood in said spent dialysate, analyzing and establishing the components and acidity of said spent dialysate therein, adjusting said component concentrations to approximately the concentration of each said component in said fresh dialysate, restoring said acidity to approximately its initial value, and removing metabolic wastes from said spent dialysate.

* * * * *